United States Patent
Tout et al.

(10) Patent No.: US 9,339,248 B2
(45) Date of Patent: May 17, 2016

(54) SYSTEMS AND METHODS FOR IMAGING SINUSES

(71) Applicant: KCI Licensing, Inc., San Antonio, TX (US)

(72) Inventors: Aidan Marcus Tout, Alderbury (GB); Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 14/873,862

(22) Filed: Oct. 2, 2015

(65) Prior Publication Data

US 2016/0022234 A1 Jan. 28, 2016

Related U.S. Application Data

(62) Division of application No. 13/167,292, filed on Jun. 23, 2011, now Pat. No. 9,198,987.

(60) Provisional application No. 61/358,762, filed on Jun. 25, 2010.

(51) Int. Cl.
*A61B 6/12* (2006.01)
*A61B 6/00* (2006.01)
(Continued)

(52) U.S. Cl.
CPC ............... *A61B 6/481* (2013.01); *A61B 19/54* (2013.01); *A61K 49/04* (2013.01); *A61K 49/0409* (2013.01); *A61M 1/0088* (2013.01); *A61B 6/12* (2013.01); *A61B 2019/5433* (2013.01); *A61B 2019/5466* (2013.01); *A61B 2019/5487* (2013.01); *A61F 2013/0028* (2013.01); *A61F 2013/00174* (2013.01); *A61F 2013/00285* (2013.01); *A61F 2013/00357* (2013.01)

(58) Field of Classification Search
CPC ........... A61B 19/54; A61B 2019/5433; A61B 2019/5466; A61B 2019/5487; A61B 6/12; A61K 49/0409
See application file for complete search history.

(56) References Cited

U.S. PATENT DOCUMENTS 1,355,846 A  10/1920  Rannells
2,547,758 A   4/1951  Kelling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Mark Remaly (57) ABSTRACT

Systems, devices, and methods for imaging a sinus in a patient involving a through sinus are presented. In one instance, a system includes a radiopaque wound filler for disposing into the through sinus. The system further includes a radiopaque solution for deploying into the sinus, and a radiopaque solution unit having a radiopaque solution reservoir and a positive pressure source. Other systems, devices, and methods are presented.

13 Claims, 5 Drawing Sheets

(51) Int. Cl.
*A61B 19/00* (2006.01)
*A61K 49/04* (2006.01)
*A61M 1/00* (2006.01)
*A61F 13/00* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

SYSTEMS AND METHODS FOR IMAGING SINUSES

RELATED APPLICATIONS

This application is a divisional of U.S. patent application Ser. No. 13/167,292, entitled "Systems and Methods for Imaging Sinuses," filed Jun. 23, 2011, which claims the benefit, under 35 USC §119(e), of the filing of U.S. Provisional Patent Application No. 61/358,762, entitled "Systems and Methods For Imaging Sinuses," filed Jun. 25, 2010. Each of the applications set forth above are incorporated herein by reference for all purposes.

BACKGROUND

The present disclosure relates generally to medical treatment systems and, more particularly, but not by way of limitation, to systems and methods for imaging sinuses in a patient.

At times patients have issues with infected tracts, such as a passage between an abscess and the skin, that are known as sinuses. Techniques for treating sinuses typically rely on visual inspection of the sinus and involve the use of medical probes. Issues exist at times, however, with visualizing the sinus or sinuses adequately to allow proper treatment.

SUMMARY

According to an illustrative embodiment, a method for imaging a sinus that has a through sinus in a patient includes the steps of disposing a radiopaque wound filler into the through sinus, deploying a radiopaque solution into the sinus, and capturing a radiographic image of the sinus. The radiopaque wound filler has a patterned radiographic image. In the radiographic image, the radiopaque wound filler presents a first contrast and the radiopaque solution presents a second contrast.

According to another illustrative embodiment, a method for imaging a sinus in a patient includes the steps of using a radiopaque foaming unit to introduce a radiopaque foam into the sinus. The radiopaque foam is at least initially flowable. The method further includes capturing a radiographic image of the sinus.

According to another illustrative embodiment, a method of identifying a foreign object in a sinus of a patient includes the steps of introducing a radiopaque solution having a binding agent into the sinus and allowing the radiopaque solution to dwell in the sinus. As the radiopaque solution dwells, the foreign object absorbs the radiopaque solution. The method further includes capturing a first radiographic image of the sinus.

According to another illustrative embodiment, a system for imaging a sinus in a patient involving a through sinus includes a radiopaque wound filler for disposing into the through sinus. The radiopaque wound filler has patterned radiopaque markers that are operable to present a patterned radiographic image. The system further includes a radiopaque solution for deploying into the sinus and a radiopaque solution unit having a radiopaque solution reservoir and a positive pressure source. The radiopaque solution unit is fluidly coupled to the sinus.

According to another illustrative embodiment, a system for imaging a sinus in a patient involving a through sinus includes a radiopaque foaming unit for introducing a radiopaque foam into the sinus. The radiopaque foam is at least initially flowable. The system further includes a reduced pressure unit for fluidly coupling to the sinus. The reduced pressure unit is for supplying reduced pressure to the sinus and for receiving fluids from the sinus.

According to another illustrative embodiment, a kit for imaging a sinus in a patient involving a through sinus is provided. The kit includes a radiopaque wound filler for disposing into the through sinus. The radiopaque wound filler has patterned radiopaque markers that are operable to present a patterned radiographic image. The kit further includes a radiopaque solution for deploying into the sinus and operable, when subjected to radiography, to make a radiographic image different from the patterned radiographic image of the wound filler. The kit further includes a package for securing the radiopaque wound filler and the radiopaque solution.

Other objects and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims. Unless otherwise indicated, as used herein, "or" does not require mutual exclusivity.

Figure 1:
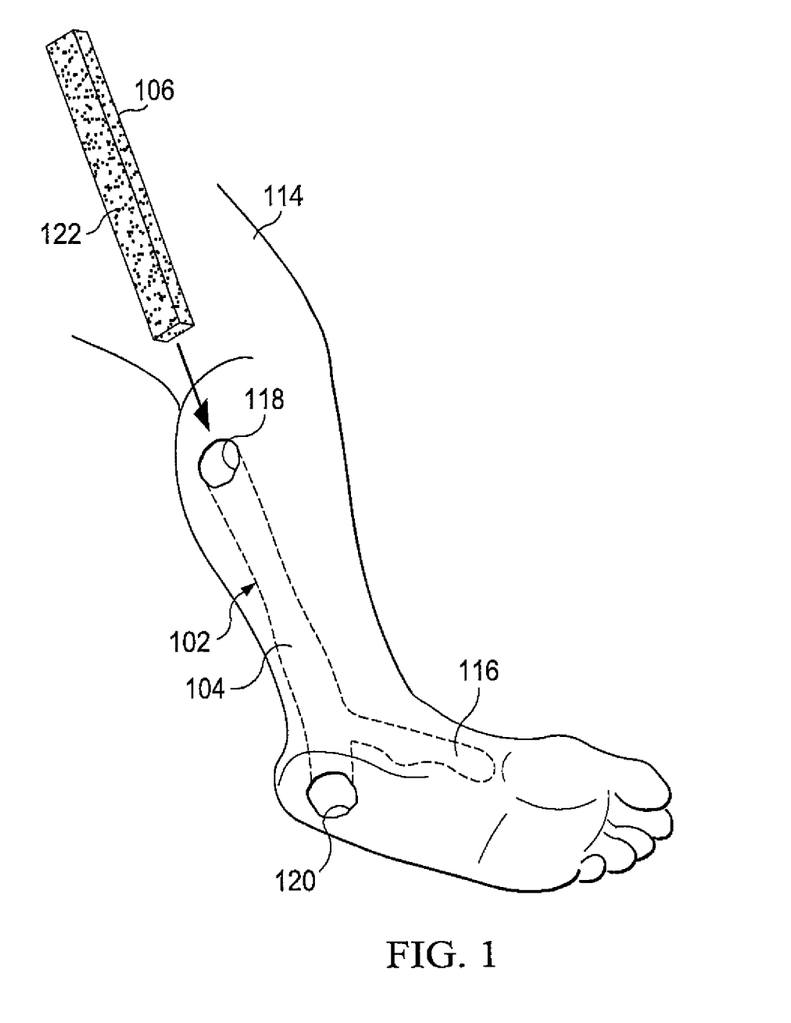
FIG. 1 is a schematic perspective view of an radiopaque wound filler being inserted into a sinus of a patient.
Figure 2:
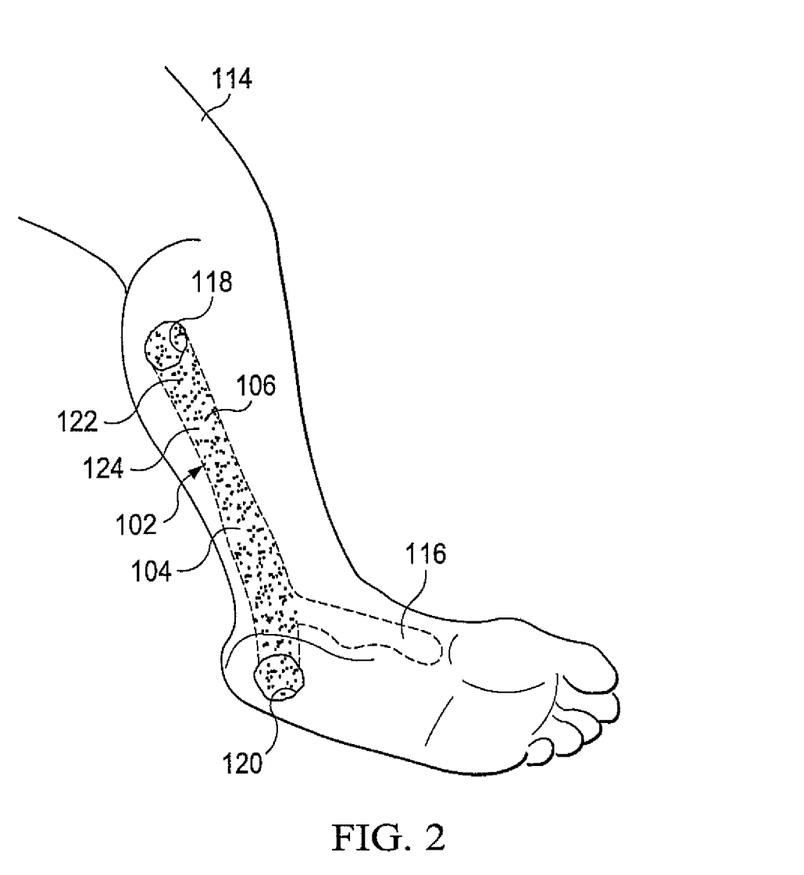
FIG. 2 is a schematic perspective view of the sinus of FIG. 1 shown with the wound filler appearing as a radiographic image.
Figure 3:
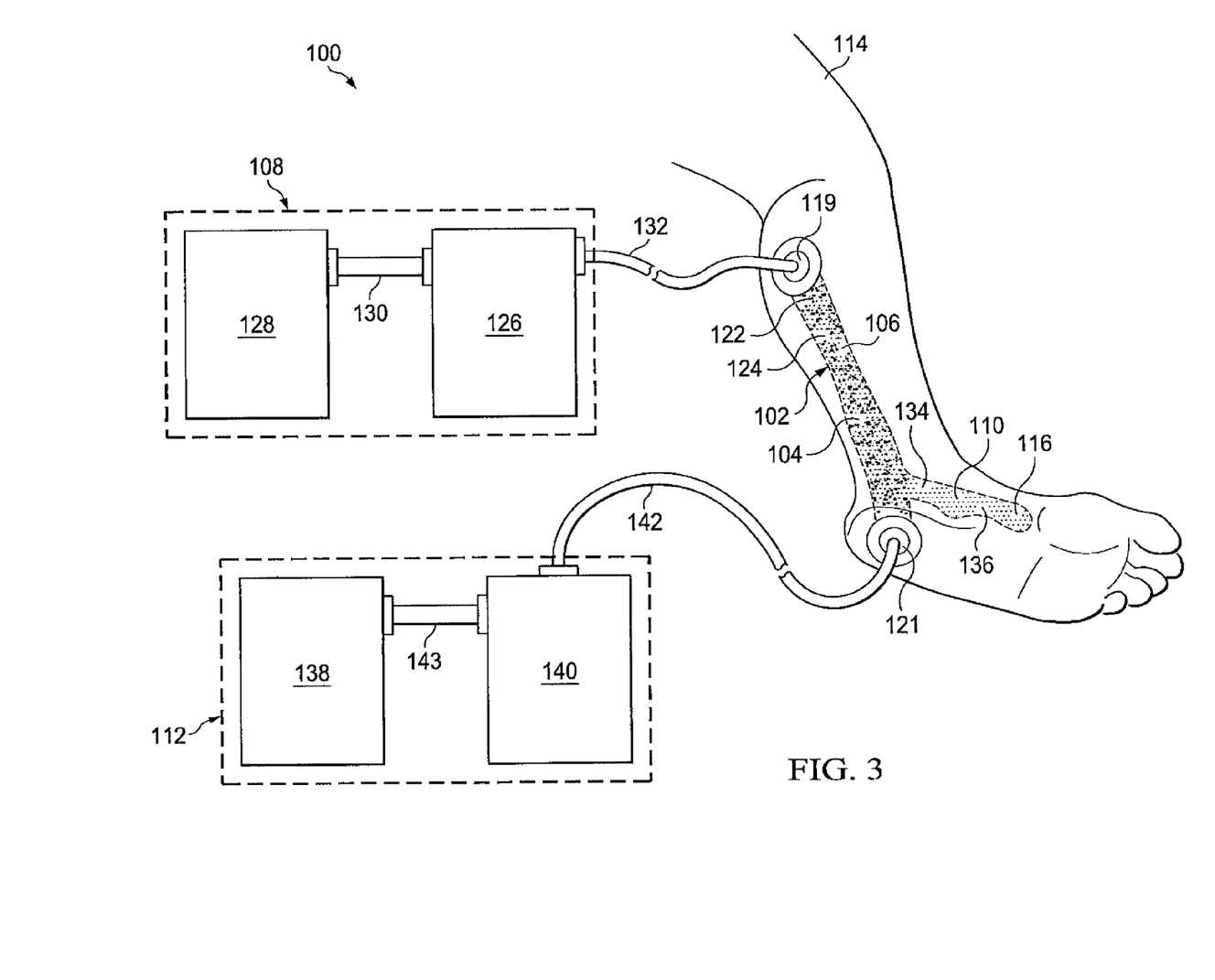
FIG. 3 is a schematic diagram, with a portion shown in perspective view, of an illustrative embodiment of system for imaging a sinus of a patient.

Referring to the drawings and primarily to FIGS. 1-3, an illustrative embodiment of a system 100 for imaging a sinus 102 of a patient is presented. The system 100 includes a radiopaque wound filler 106 for disposing into a through sinus 104, and a radiopaque solution unit 108 fluidly coupled to the sinus 102 for deploying a radiopaque solution 110 into the sinus 102. The system 100 may further include a reduced pressure unit 112 fluidly coupled to the sinus 102 for applying reduced pressure to the sinus 102. The application of the radiopaque wound filler 106 and the radiopaque solution 110 into the sinus 102 may help enable accurate assessments of complex wound structures having tortuous sinuses that may be transiently connected or that may otherwise be difficult to detect through the use of conventional sinogram imaging.

A sinus is generally any course or path of tissue destruction extending from a patient's epidermis 114 (i.e., skin) that creates dead space or cavities. The sinus may be in any direction underneath the epidermis 114 and may create the potential for abscess formation. The sinus 102 may further comprise a cavity or hollow in the body, such as a narrow elongated track extending from the patient's epidermis 114. The sinus may involve one or more tissue sites. For example, the sinus 102 may connect to the surface or edge of one or more wounds. A wound is on a tissue site, and in general, a tissue site may be the bodily tissue of any human, animal, or other organism, including bone tissue, adipose tissue, muscle tissue, dermal tissue, vascular tissue, connective tissue, cartilage, tendons, ligaments, or any other tissue.

The sinus 102 may have a tortuous structure comprising a network of cavities. Certain areas of the sinus may be transiently open to the network or may angle off to form a hidden sinus. Thus, in the illustrative embodiment, the sinus 102 may include the through sinus 104 and a hidden sinus 116. The through sinus 104 may be relatively straight. For example, a probe (not shown) used by a healthcare provider could pass from a first opening 118 of the sinus 102, via the through sinus 104, to a second opening 120 of the sinus 102. The hidden sinus 116 may branch off from the through sinus 104 making the hidden sinus 116 difficult to locate and assess. In some instances, the hidden sinus 116 may only be transiently open to the through sinus 104. The transient opening may make it difficult to determine the hidden sinus' 116 existence. Should a healthcare provider be unaware of the hidden sinus' 116 existence, the healthcare provider may fail to properly treat the hidden sinus 116, and thus, potentially allow an infection in the hidden sinus 116 to compromise the treatment of the sinus 102. The through sinus 104 is typically a sinus 102 going from a first opening 118 to a second opening 120, but may also be a tract with one opening.

The radiopaque wound filler 106 may be sized and deployed into the through sinus 104 via the first opening 118 or the second opening 120 of the sinus 102. The radiopaque wound filler 106 may refer to devices that have structural elements arranged to form flow channels, such as, for example, cellular foam and open-cell foam. The radiopaque wound filler 106 may be porous and may be made from foam, gauze, felted mat, or any other material suited to a particular biological application. In one embodiment, the radiopaque wound filler 106 is a porous foam and includes a plurality of interconnected cells or pores that act as flow channels. The porous foam may be a polyurethane, open-cell, reticulated foam, such as GranuFoam® material manufactured by Kinetic Concepts, Incorporated of San Antonio, Tex.

The radiopaque wound filler 106 may further function as a manifold for purposes of applying reduced pressure. Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently. Consistent with the use herein, unless otherwise indicated, an increase in reduced pressure or vacuum pressure typically refers to a reduction in absolute pressure. Positive pressure generally refers to a pressure greater than ambient pressure at a tissue site that is being subjected to treatment.

The radiopaque wound filler 106 may function as a manifold. Manifold generally refers to a substance or structure that is provided to assist in applying reduced pressure to, delivering fluids to, or removing fluids from a tissue site, such as the sinus 102. A plurality of flow channels or pathways in the radiopaque wound filler 106 may help distribute fluids provided to and removed from the sinus 102 around the radiopaque wound filler 106. In one illustrative embodiment, the flow channels or pathways are interconnected to improve distribution of fluids provided or removed from the radiopaque wound filler 106. In some situations, the radiopaque wound filler 106 may also be used to distribute fluids, such as medications, antibacterials, growth factors, and various solutions to the sinus 102.

The radiopaque wound filler 106 includes a first radiopaque marker 122 that may coat the radiopaque wound filler 106 or be imbedded in or attached to the radiopaque wound filler 106 or otherwise associated with the radiopaque wound filler 106. While the whole of the radiopaque wound filler 106 may not be radiopaque, it often is.

The radiopaque wound filler 106 is porous and may be formed from a reticulated foam. The foam may be made from polyurethane (PU), which is made by mixing monomers together along with a foaming agent. The radio opaque agent(s) or markers, e.g., markers 122, 134, may be added to the monomers prior to mixing and foaming the polyurethane foam. The polyurethane foam may be made in a range of densities (16-64 kg/m$^3$) and porosities (15 pores per inch (ppi)-200 ppi)).

The formed polyurethane foam used to form the radiopaque wound filler 106 may be further heated and compressed to form a felted foam where the density of the foam may be increased by up to six times. The polyurethane foam may also have the radio opaque material coated onto its surface, for example by plasma treatment where the coating is chemically grafted to a substrate of the polyurethane foam. The radiopaque wound filler 106 may be cut, die cut, or routed from the foam in rods of various dimensions (e.g., a length up to 1 m, diameter up to 5 cm), where the cross sectional shape of each rod is typically circular, but could also be square, or star shaped, or other shapes. In addition, there could be grooves or slits formed into the length of the rod. Other polymer foams may be formed from solutions or from the melt.

The radiopaque wound filler 106 may also be formed from a sintered polymer material (see, e.g., POREX materials from Porex Technologies of Fairburn, Ga., U.S.A. (www.porex.com), or FILTRONA materials from Filtrona plc of Milton Keynes, United Kingdom (www.filtrona.com)). To create the radiopaque wound filler 106 with this approach, polymer granules are compressed and heated to form porous sheets and simple geometric shapes (such as rods described above). The polymer may be premixed with radio opaque material before sintering, or the fully sintered polymer form may be coated using plasma coating as described above or another technique.

Suitable polymer materials for use herein include the following: Polyurethane, vinyl acetate homo and copolymers, acrylics, polyolefins, polyesters, polyamides, thermoplastic elastomers, silicones, and fluoropolymers. Suitable materials for the radio opaque markers, e.g., radio opaque markers 122, 134, include compounds containing barium sulphate (barytes) or iodine and its compounds. For example, an iodine modified acrylic monomer could be used as a precursor for plasma-based coating of the marker material.

The first radiopaque marker 122 may be arranged in or on the radiopaque wound filler 106 to present a distinctive pattern that is visible in a sinogram image, or radiographic image, i.e., the first radiopaque marker 122 presents a patterned radiographic image. The first radiopaque marker 122 may be a spaced plurality of radiopaque markers or materials that form what may be referred to as patterned radiopaque markers. The first radiopaque marker 122 presents a first contrast 124 or distinctive image on a radiographic image. The first contrast 124 allows the location of the first radiopaque marker 122 to be seen on the radiographic image. The sinogram image may be created, for example, from computed tomography scans (CT scans), magnetic resonance imaging (MRI), ultrasound (US), or x-rays. For illustration purposes, the first radiopaque marker 122 and the first contrast 124 are shown in FIG. 2 as they might appear on a sinographic image. The radiopaque wound filler 106 is, thus, operable to present a patterned sinogram image when a sinogram is taken.

Referring now to FIG. 3, the radiopaque solution unit 108 includes a radiopaque solution reservoir 126 that contains the radiopaque solution 110. The radiopaque solution unit 108 may also include a positive pressure source 128 for delivering the radiopaque solution 110 to the sinus 102. The positive pressure source 128 may be fluidly coupled by a first conduit 130 to the radiopaque solution reservoir 126 to deliver positive pressure to the radiopaque solution reservoir 126. The positive pressure source 128 may cause the radiopaque solution 110 to be delivered via a second conduit 132 to the first opening 118 of the sinus 102. The radiopaque solution unit 108 may utilize any device or structure for delivering the radiopaque solution 110 to the sinus 102. The radiopaque solution 110 may be applied to the first opening 118 of the sinus 102 continuously or intermittently.

The radiopaque solution 110 includes a second radiopaque marker 134 that may be visible in a sinogram image as shown in FIG. 3. The second radiopaque marker 134 may present a second contrast 136 distinct from the first contrast 124. The radiopaque markers 122, 134 may include spaced metallic material, barium compounds, iodine compounds, graphene liquid, bismuth compounds such as bismuth subcarbonate, or other radiopaque materials. For example, without limitation, the radiopaque markers 122, 134 or patterned radiographic markers may be spaced metallic material or spaced graphene material in or on the radiopaque wound filler 106. For illustrative purposes, the radiopaque markers 122 and 134 and contrasts 124 and 136 are shown in FIG. 3 as they might appear on a sinogram image.

As previously noted, the reduced pressure unit 112 may be fluidly coupled to the sinus 102 for applying reduced pressure to the sinus 102. The reduced pressure unit 112 may include a reduced pressure source 138 fluidly coupled to a collection reservoir 140. A first reduced pressure delivery conduit 142 provides fluid communication between the second opening 120 of the sinus 102 and the collection reservoir 140. Liquids or exudates communicated from the second opening 120 through the first reduced pressure delivery conduit 142 are removed from the first reduced pressure delivery conduit 142 and retained within the collection reservoir 140. A second reduced pressure delivery conduit 143 may fluidly couple the collection reservoir 140 to the reduced pressure source 138. The reduced pressure unit 112 may be any device, structure, or technique for delivering reduced pressure to the sinus 102. The reduced pressure may be applied to the second opening 120 of the sinus 102 continuously or intermittently.

In an alternative illustrative embodiment (not explicitly shown), the sinus 102 may include only the first opening 118 and both the radiopaque solution unit 108 and the reduced pressure unit 112 may be fluidly coupled to the first opening 118 to deliver the radiopaque solution 110 and the reduced pressure to the first opening 118. The radiopaque solution 110 and the reduced pressure may be applied in sequence.

In one illustrative embodiment, a method for imaging the sinus 102 that includes or involves the through sinus 104 in a patient includes disposing the radiopaque wound filler 106 into the through sinus 104. The healthcare provider may dispose the radiopaque wound filler 106 into the through sinus 104 by sizing the radiopaque wound filler 106 and inserting the radiopaque wound filler 106 into the first opening 118 or the second opening 120 of the sinus 102. The healthcare provider may fluidly couple the radiopaque solution unit 108 to the first opening 118 using the second conduit 132. A first interface 119 may be used to facilitate forming a seal over the first opening 118 while allowing fluid communication between the second conduit 132 and the sinus 102. The radiopaque solution 110 may be introduced or deployed into the first opening 118 using positive pressure, by pulling the radiopaque solution 110 with reduced pressure delivered through a second interface 121, or by any other technique. A sinogram image, or radiographic image, of the sinus 102 is then captured. In the sinographic image, the radiopaque wound filler 106 presents the first contrast 124 and the radiopaque solution 110 presents the second contrast 136 as shown clearly in FIG. 3.

Using the contrasts 124, 136 in one or more sinogram images, or radiographic images, the healthcare provider may identify the hidden sinus 116 by locating areas having the second contrast 136 without the first contrast 124. Additionally, the healthcare provider may optimize the placement of the radiopaque wound filler 106 in the sinus 102 and monitor the healing progression of the tissue site based on the results of the one or more sinogram images. The healthcare provider may also determine the volume of the sinus 102 by using two or more sinogram images having different orientations to calculate the volume of the sinus 102.

The healthcare provider may further fluidly couple the reduced pressure unit 112 to the second opening 120 of the sinus 102 and apply reduced pressure to the sinus 102. The second interface 121 may used to provide a fluid seal over the second opening 120 while allowing fluid communication between the first reduced pressure delivery conduit 142 and the sinus 102. Reduced pressure may be distributed via the radiopaque wound filler 106.

Figure 4:
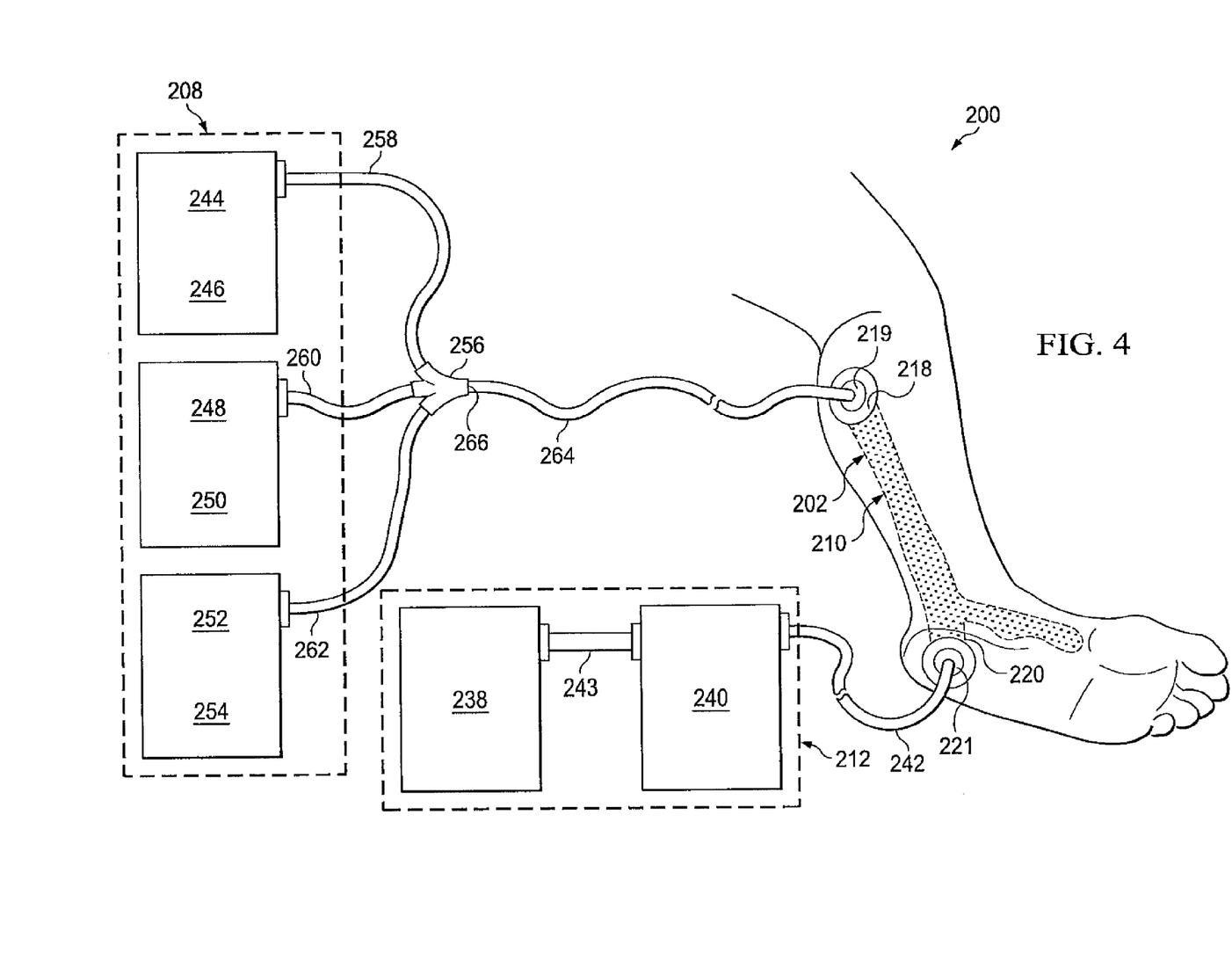
FIG. 4 is a schematic diagram, with a portion shown in perspective, of another illustrative embodiment of a system for imaging a sinus of a patient.

Referring now primarily to FIG. 4, another illustrative embodiment of a system 200 for imaging a sinus 202 of a patient is presented. The system 200 includes a radiopaque foaming unit 208 for introducing a radiopaque foam 210 into the sinus 202. The system 200 may further include a reduced pressure unit 212 fluidly coupled to the sinus 202 for applying reduced pressure to the sinus 202. The introduction of the radiopaque foam 210 into the sinus 202 may help enable accurate assessments of complex wound structures having tortuous sinuses that may be transiently connected. The radiopaque foam 210 may expand or push into areas of the sinus 202 that would otherwise be closed at the time of treatment. One or more sinogram images may be recorded.

The radiopaque foaming unit 208 may include a first fluid source 244 containing a first fluid 246, a second fluid source 248 containing a second fluid 250, and a radiopaque solution source 252 containing a radiopaque solution 254. The fluid sources 244, 248, and the radiopaque solution source 252 are fluidly coupled to a coupler 256 via conduits 258, 260, and 262, respectively. The coupler 256 is fluidly coupled by a conduit 264 to a first opening 218 of the sinus 202. A first interface 219 may be disposed over the first opening 218 to provide a fluid seal while allowing fluid communication between the conduit 264 and the sinus 202. The first fluid 246, the second fluid 250, and the radiopaque solution 254 produce the radiopaque foam 210 when mixed. The radiopaque foam 210 is at least initially flowable.

The first fluid 246, the second fluid 250, and the radiopaque solution 254 may be mixed in a mixing area 266 in or near the coupler 256. The mixing area 266 may be the coupler 256 or the coupler 256 and the conduit 264. In an alternative embodiment (not explicitly shown), the mixing area 266 may be at the first opening 218 or in the sinus 202 itself. In one illustrative embodiment, the radiopaque solution 254 may be premixed into the first fluid 246 or the second fluid 250.

The first fluid 246 and the second fluid 250 may be any fluids that when combined create a temporary or permanent foam. For example, the first fluid 246 may be an acidic solution, and the second fluid 250 may be a basic solution. In specific, non-limiting embodiments, the first fluid 246 may comprise citric acid, acetic acid, hypochlorous acid, ascorbic acid, or benzoic acid. The second fluid 250 may include sodium bicarbonate, hydrogen peroxide, and carbonic acid. The first and second fluids 246, 250 may include a surfactant configured to stabilize the radiopaque foam 210. The radiopaque foam 210 may include gas comprising between 10 and 99 percent volume of the radiopaque foam 210.

As previously noted, the system 200 may further include the reduced pressure unit 212 that is fluidly coupled to the sinus 202 for applying reduced pressure to the sinus 202. The reduced pressure unit 212 may include a reduced pressure source 238 fluidly coupled to a collection reservoir 240. A reduced pressure delivery conduit 242 may provide fluid communication between a second opening 220 of the sinus 202 and the collection reservoir 240. A second interface 221 may be disposed over the second opening 220 to provide a fluid seal and yet to allow fluid communication between the reduced pressure delivery conduit 242 an the sinus 202.

Liquids or exudates communicated from the second opening 220 through the reduced pressure delivery conduit 242 are removed from the reduced pressure delivery conduit 242 and delivered to the collection reservoir 240. A reduced pressure delivery conduit 243 may fluidly couple the collection reservoir 240 and the reduced pressure source 238. As before, the reduced pressure unit 212 and the radiopaque foaming unit 208 may be applied to the same opening, either first opening 218 or second opening 220, and applied sequentially. When applied to the first opening 218 and the second opening 220, the radiopaque foaming unit 208 and the reduced pressure unit 212 may be applied simultaneously and continuously in some embodiments.

In some illustrative embodiments, the radiopaque foam 210 may serve to both facilitate making sinograms and facilitate applying reduced pressure. The radiopaque foam 210 may behave in a manner similar to solid wound filling foams. The radiopaque foam 210 may expand into the sinus 202 so that a radiographic image may be captured and may have characteristics to allow the radiopaque foam 210 to be used for reduced pressure application. For example, the radiopaque foam 210 may be a self-reticulating foam, such as one created by the use of blowing agents that release gases at rates capable of bursting foam cells and a controlled viscosity liquid. In addition, liquids or solids may be incorporated into the radiopaque foam 210 for additional support, delivery of medicine or other liquids, or enhanced sinograms.

In an illustrative embodiment, a method for imaging the sinus 202 in a patient includes causing the first fluid 246, the second fluid 250, and the radiopaque solution 254 to enter the mixing area 266 and the sinus 202. The method may include mixing the first fluid 246, the second fluid 250, and the radiopaque solution 254 in the mixing area 266 to create the radiopaque foam 210 and then causing the radiopaque foam 210 to flow into the sinus 202. Alternatively, the mixing area 266, where the mixing occurs, may be in the sinus 202. One or more sinogram images, or radiographic images, of the sinus 202 are captured.

Referring still to FIG. 4, but in regard to an alternative illustrative embodiment (not explicitly shown), the radiopaque foaming unit 208 may include the first fluid source 244 having a radiopaque, foamable solution. The radiopaque, foamable solution may include radio opaque materials of the types previously described. The radiopaque, foamable solution may be formed from a two-part (e.g., part A and part B) alginate mix such that when both parts are mixed, the initially-mobile alginate forms a gel. Part A of the alginate mix may be a blowing agent, such as a bicarbonate, and part B may be a weal acid, such as citric acid. When the two parts are mixed, a gelling process begins. In addition, carbon dioxide is generated to form the foam.

Rather than the chemical blowing agent system just described, a mechanical foam generation may also be used. With mechanical foam generation, parts A and B of the alginate mix as passed through an aeration mixer before being delivered to the sinus.

The radiopaque foaming unit 208 may include a foaming mechanism for generating a radiopaque foam from the radiopaque, foamable solution. The radiopaque foam may be instilled into the first opening 218 via a conduit, such as the conduit 264.

The foaming mechanism may be a mechanical agitator that includes one or more rotating elements that generates the radiopaque foam when placed in contact with the radiopaque, foamable solution. In a specific, illustrative, non-limiting embodiment the foaming mechanism may include an electric motor operable to rotate a shaft with paddles or other shaft extensions that contact the radiopaque, foamable solution during operation. Alternatively, the foaming mechanism may include an injector for injecting a gas into the first fluid source 244 to generate the radiopaque foam. In another specific, non-limiting, illustrative embodiment, the foaming mechanism may include a reservoir of pressurized air and a nozzle configured to direct the pressurized air into the first fluid source 244.

Figure 5:
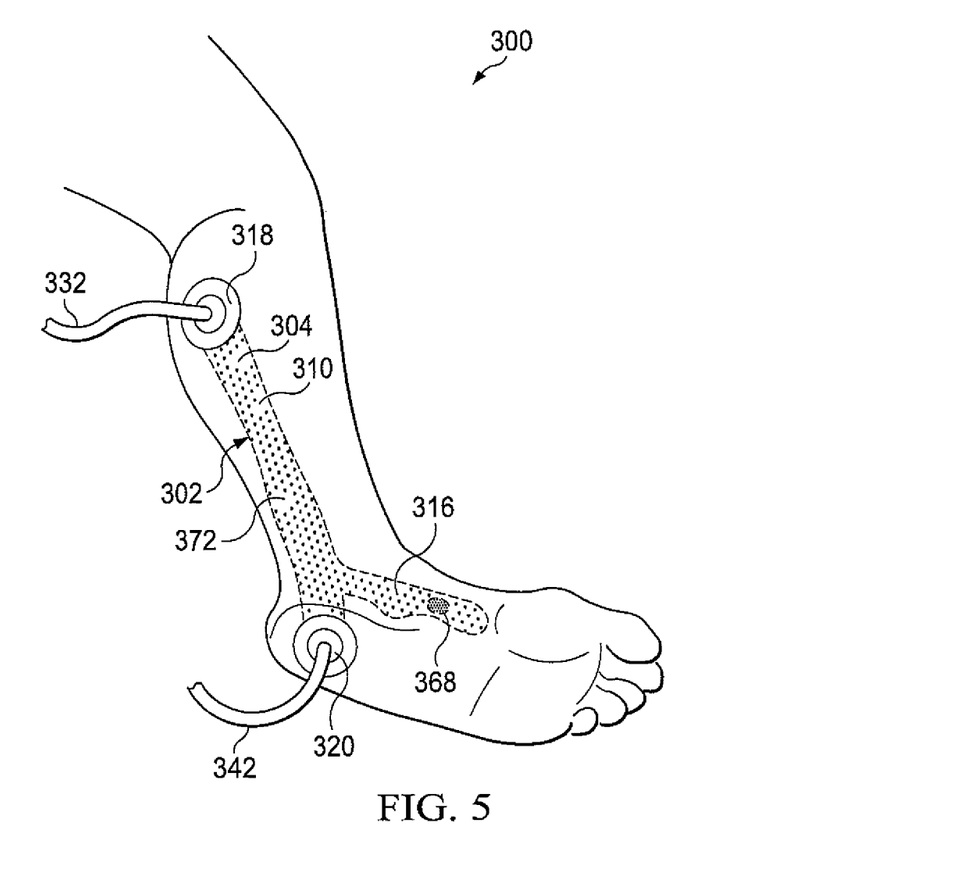
FIG. 5 is a schematic perspective view of a portion of an illustrative embodiment of a system for imaging a sinus having a foreign object.

Referring now primarily to FIG. 5, an illustrative embodiment of a system 300 for imaging a sinus 302 to identify a foreign object 368 in a patient is presented. The system 300 may include a radiopaque solution unit (not shown but analogous to those previously presented) fluidly connected to the sinus 302 via a conduit 332. The radiopaque solution unit is for disposing a radiopaque solution 310 into the sinus 302. The system 300 may further include a reduced pressure unit (not shown but analogous to those previously presented) that is fluidly coupled to the sinus 302 via a reduced pressure delivery conduit 342. The reduced pressure unit is for applying reduced pressure to the sinus 302. The sinus 302 includes a through sinus 304 and a hidden sinus 316. As shown, the foreign object 368 may be present in the hidden sinus 316.

The radiopaque solution unit may introduce the radiopaque solution 310 into a first opening 318 of the sinus 302 and may include one or more binding agents (not shown), e.g., carboxymethyl cellulose and its salts. The radiopaque solution 310 dwells in the sinus 302. Dwell means the radiopaque solution 310 is in the sinus 302 over a period of time regardless of whether the radiopaque solution 310 is static or moving. The one or more binding agents adheres to a sinus wall 372, the foreign object 368, or any infectious materials (not explicitly shown). The one or more binding agents may also build-up in the sinus 302 over time.

The reduced pressure unit may be fluidly connected to a second opening 320 of the sinus 302 for applying reduced pressure to the sinus 302 and receiving fluids from the sinus 302. The reduced pressure unit may be analogous to the reduced pressure units previously presented.

In one illustrative embodiment, a method for identifying the foreign object 368 in the sinus 302 of a patient includes introducing the radiopaque solution 310 having the binding agent into the sinus 302. The radiopaque solution 310 is allowed to dwell in the sinus 302. The foreign object 368 absorbs the radiopaque solution 310 and may absorb more (or different amount) than other tissue or items in the sinus 302 to facilitate identification. Then a first radiographic image, or first sinographic image, of the sinus 302 is captured. The step of capturing the first sinographic image may include capturing the first sinographic image after a first elapsed time ($t_1$), and further include capturing a second sinographic image of the sinus 302 after a second elapsed time ($t_2$). The foreign object 368 may show a greater contrast when the first sinographic image and the second sinographic image are compared.

The radiopaque solution 310 may be introduced into the sinus 302 intermittingly over a period of time or may be continuously introduced into the sinus 302. Over a course of treatments, the radiopaque solution 310 may build-up in the sinus 302. Additionally, introducing the radiopaque solution 310 over a period of time may provide the opportunity for the radiopaque solution 310 to reach into areas of the sinus 302 that may have been previously closed, e.g., a hidden sinus, such as the hidden sinus 316 which may be intermittently closed to the through sinus 304. A sinographic image may show a greater contrast between the through sinus 304 and the hidden sinus 316 as the through sinus 304 may have a higher concentration of the binding agent than the transiently closed hidden sinus, e.g., the hidden sinus 316. The foreign object 368 may absorb the most radiopaque solution 310 or at least a differing amount that allows a contrast.

In another embodiment, a kit may be formed that facilitates the imaging of a sinus. The kit includes a radiopaque wound filler for disposing into the through sinus. The radiopaque wound filler may be any of the types previously described. The radiopaque wound filler has patterned radiopaque markers that are operable to present a patterned radiographic image. The kit further includes a radiopaque solution for deploying into the sinus and operable, when subjected to radiography, to make a radiographic image different from the patterned radiographic image of the wound filler. The kit further includes a package for securing the radiopaque wound filler and the radiopaque solution. The package may be for example a formed polymer tray that receives the foam into a shelf and has a sealed vial containing the radiopaque solution. The vial may be received into a portion of the package using an interference fit. The kit may further include a radiopaque solution unit as previously described.

Although the present invention and its advantages have been disclosed in the context of certain illustrative embodiments, it should be understood that various changes, substitutions, permutations, and alterations can be made without departing from the scope of the invention as defined by the appended claims. As an illustrative example, components from one illustrative embodiment may be used with components from another embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for imaging a sinus that includes a through sinus in a patient, the method comprising:
    disposing a radiopaque wound filler into the through sinus, wherein the radiopaque wound filler includes a first radiopaque marker to present a first contrast in a sinographic image;
    deploying a radiopaque solution into the sinus; and
    capturing a sinographic image of the sinus in which the first radiopaque marker of the radiopaque wound filler presents the first contrast and the radiopaque solution presents a second contrast.

2. The method of claim 1, further comprising identifying a hidden sinus by identifying areas having the second contrast and not the first contrast.

3. The method of claim 1, further comprising applying reduced pressure to the sinus.

4. The method of claim 1, wherein:
    the step of deploying the radiopaque solution comprises introducing the radiopaque solution using positive pressure;
    wherein the radiopaque wound filler comprises a reduced pressure manifold; and
    further comprising applying reduced pressure to the sinus.

5. The method of claim 4, wherein the sinus has a first opening and a second opening, and wherein the radiopaque solution is introduced through the first opening and the reduced pressure is introduced through the second opening.

6. The method of claim 4, wherein the sinus has a first opening and wherein the radiopaque solution is introduced through the first opening and the reduced pressure is introduced through the first opening.

7. A method for imaging a sinus in a patient, the method comprising:
    using a radiopaque foaming unit to introduce a radiopaque foam into the sinus, wherein the radiopaque foam is at least initially flowable; and
    capturing a sinographic image of the sinus.

8. The method of claim 7, wherein the radiopaque foaming unit comprises:
    a first fluid source containing a first fluid;
    a second fluid source containing a second fluid;
    a radiopaque solution source containing a radiopaque solution;

a mixing area fluidly coupled to the first fluid source, the second fluid source, and the radiopaque solution source; and wherein the radiopaque foaming unit is operable to produce the radiopaque foam when the first fluid, the second fluid, and the radiopaque solution are mixed.

9. The method of claim 7, wherein the step of using the radiopaque foaming unit comprises:
   introducing a first fluid into a mixing area;
   introducing a second fluid into the mixing area;
   introducing a radiopaque solution into the mixing area;
   mixing the first fluid, the second fluid, and the radiopaque solution in the mixing area to create the radiopaque foam; and
   causing the radiopaque foam to flow into the sinus.

10. The method of claim 7, wherein the radiopaque foaming unit comprises a first fluid source containing a radiopaque, foamable solution and an agitator.

11. The method of claim 7, wherein the radiopaque foaming unit comprises a first fluid source containing a radiopaque, foamable solution and a gas injector for causing the radiopaque, foamable solution to foam.

12. A method of identifying a foreign object in a sinus of a patient, the method comprising the steps of:
   introducing a radiopaque solution having a binding agent into the sinus;
   allowing the radiopaque solution to dwell in the sinus, wherein the radiopaque solution attaches to the foreign object; and
   capturing at least one sinographic image of the sinus.

13. The method of claim 12, wherein the step of capturing the at least one sinographic image comprises capturing a first sinographic image after a first elapsed time ($t_1$) and further comprising capturing a second sinographic image of the sinus after a second elapsed time ($t_2$), wherein the foreign object shows a greater contrast between the first sinographic image and the second sinographic image.

* * * * *